United States Patent
Silverstein et al.

Patent Number: 6,035,229
Date of Patent: Mar. 7, 2000

[54] METHOD AND APPARATUS FOR DETECTING BARRETT'S METAPLASIA OF THE ESOPHAGUS

[75] Inventors: Fred E. Silverstein, Seattle; Roy W. Martin, Redmond; Darik Taniguchi, Bothell; John A. Myers, Seattle, all of Wash.

[73] Assignee: Washington Research Foundation, Seattle, Wash.

[21] Appl. No.: 08/878,227

[22] Filed: Jun. 17, 1997

Related U.S. Application Data

[63] Continuation of application No. 08/274,965, Jul. 14, 1994, abandoned.

[51] Int. Cl.[7] .................................................. A61B 5/00
[52] U.S. Cl. ......................... 600/473; 600/117; 600/341
[58] Field of Search .................. 600/473–478, 600/117, 341-3

[56] References Cited

U.S. PATENT DOCUMENTS

| | | | |
|---|---|---|---|
| 3,913,568 | 10/1975 | Carpenter | 128/11 |
| 4,467,812 | 8/1984 | Stoller | 128/664 |
| 4,593,313 | 6/1986 | Nagasaki et al. | 358/98 |
| 4,616,657 | 10/1986 | Stoller | 128/664 |
| 4,651,743 | 3/1987 | Stoller | 128/664 |
| 4,768,089 | 8/1988 | Kato | 358/98 |
| 4,802,487 | 2/1989 | Martin et al. | 600/109 |
| 4,819,077 | 4/1989 | Kikuchi et al. | 358/98 |
| 4,885,634 | 12/1989 | Yabe | 358/98 |
| 4,914,512 | 4/1990 | Sekiguchi | 358/98 |
| 4,934,339 | 6/1990 | Kato | 128/6 |
| 4,998,973 | 3/1991 | Kikuchi | 600/117 |
| 5,092,331 | 3/1992 | Nakamura et al. | 128/634 |
| 5,105,269 | 4/1992 | Nakamura et al. | 358/98 |
| 5,357,954 | 10/1994 | Shigezawa | 128/634 |
| 5,381,786 | 1/1995 | Speccs | 600/117 |
| 5,396,880 | 3/1995 | Kagan et al. | 600/117 |
| 5,421,337 | 6/1995 | Richards-Kortum | 128/665 |

FOREIGN PATENT DOCUMENTS

| | | |
|---|---|---|
| 0 049 905 | 4/1982 | European Pat. Off. . |
| 0 323 816 A1 | 7/1989 | European Pat. Off. ....... G01N 21/31 |
| 30 38 786 | 4/1982 | Germany . |
| 38 44 651 C2 | 8/1990 | Germany . |
| 60-136521 | 7/1985 | Japan . |
| 63-54144 | 3/1988 | Japan . |
| 64-5526 | 1/1989 | Japan . |
| 2-35358 | 2/1990 | Japan . |
| 1428352 | 10/1988 | U.S.S.R. . |
| 90/14858 | 12/1990 | WIPO . |

OTHER PUBLICATIONS

Schuman, B. M., "Premalignant lesions of the gastrointestinal tract," *Postgraduate Medicine*, 91:2, Feb. 1, 1992.

*Primary Examiner*—Robert L. Nasser
*Attorney, Agent, or Firm*—Seed Intellectual Property Law Group PLLC

[57] ABSTRACT

A system for detecting Barrett's metaplasia utilizes an illumination and imaging probe at the end of a catheter. The probe illuminates the wall of the esophagus and returns reflected light to be processed to provide a visual indication of the color of the esophageal wall. The position of the probe along the length of the esophagus is also measured to allow a medical practitioner to determine the location of the transition from the pink stomach lining to the white esophageal lining.

17 Claims, 8 Drawing Sheets

METHOD AND APPARATUS FOR DETECTING BARRETT'S METAPLASIA OF THE ESOPHAGUS

CROSS-REFERENCE TO RELATED APPLICATION

The application is a continuation of U.S. patent application Ser. No. 08/274,965, filed Jul. 14, 1994, now abandoned.

TECHNICAL FIELD

This invention relates to medical diagnostic devices, and more particularly, to a method and apparatus for observing the esophageal wall and measuring the position of colorimetric changes to diagnose Barrett's metaplasia.

BACKGROUND OF THE INVENTION

Chronic reflux (heartburn) damages the lining of the esophagus by repeatedly exposing it to stomach acid This damage is believed to lead to the replacement of the normal stratified squamous esophageal lining with a columnar mucosal tissue. The conversion of the normal lining tissue to columnar tissue is called Barrett's metaplasia.

Barrett's metaplasia is a precursor and an important risk factor for cancer of the esophagus. About 25 million Americans suffer persistent chronic heartburn, and 10% of those will develop Barrett's metaplasia. Patients with Barrett's metaplasia are from 10 to 125 times more likely to develop cancer of the esophagus than the general population Cancer of the esophagus is fairly common, with about 30,000 cases per year currently reported in the United States. Cancer of the esophagus is also deadly, with a five-year survival rate of about 7%.

Currently, Barrett's metaplasia is diagnosed by endoscopy once symptoms have become severe enough to demand endoscopy examination However, at this point, about 5% to 10% of the patients endoscopically examined and found to have Barrett's metaplasia already have cancer of the esophagus. Unfortunately, endoscopic examination for Barrett's metaplasia is too expensive and time-consuming for routine mass screening of patients suffering persistent chronic heartburn. If a feasible and cost-effective technique could be developed for detecting Barrett's metaplasia before it has progressed to cancer of the esophagus, it would be possible to monitor patients with Barrett's metaplasia periodically, such as every six months to two years, to detect a transition to precancer (dysplasia) or to esophageal cancer at an early stage. Early detection of esophageal cancer would improve the rate of survival because esophageal cancer, when diagnosed at an early stage, is more likely to be surgically curable than when diagnosed at an advanced stage.

The lining of a normal esophagus is pearly white, while the lining of a normal stomach is salmon pink. The white-to-pink junction normally occurs at a depth of 39 to 41 cm from the teeth of a patient In patients with Barrett's metaplasia, the white-to-pink junction may occur 21 to 25 cm from the teeth of the patient. At this level the color changes from white to pink, a junction called the ora serrata. The abnormally high location of this transition is normally used to diagnose Barrett's metaplasia during endoscopic examinations. If the ora serrata is located unusually high in the esophagus, biopsies are taken of the lining below the ora serrate. These biopsies are examined with a microscope to make a diagnosis of Barrett's metaplasia. The endoscopic examination must be performed carefully by a highly trained and experienced endoscopist. It is not currently realistic to attempt to screen all patients with heartburn endoscopically because of limitations in personnel, time involved in cleaning the endoscope and expense.

In summary, there is currently no quick, relatively inexpensive screening technique that could be used by relatively untrained medical practitioners to detect Barrett's metaplasia. As a result, no feasible and cost-effective means currently exist for the mass screening of reflux esophagitis patients in order to detect Barrett's metaplasia

SUMMARY OF THE INVENTION

It is an object of the invention to provide a method and apparatus for detecting Barrett's metaplasia that is sufficiently quick and inexpensive that it can be used for mass screening of potential Barrett's metaplasia.

It is another object of the invention to provide a method and apparatus for detecting Barrett's metaplasia that can effectively be used by relatively untrained medical practitioners.

It is still another object of the invention to provide a method and apparatus for detecting Barrett's metaplasia with a great deal of accuracy.

These and other objects of the invention are provided by a system including a probe mounted at a distal end of a flexible catheter. The probe includes an illuminator and a light receiving device each of which are directed radially outward toward the esophageal wall. As a result, the illuminator and a light receiving device illuminate the esophageal wall, and receive light from the esophageal wall. A sensing device coupled to the light receiving device provides an indication of the color of the esophageal wall The light from the illuminator is preferably of a color other than red, such as blue or green, so that the red or salmon pink esophageal wall will not significantly reflect the illuminator's light, but rather absorb it As a result, the intensity of light reflected from a normal white esophageal wall will be significantly different from the intensity of light reflected from an abnormal pink esophageal wall. However, full color spectrum sensing or imaging can also be used.

In use, the probe is inserted into the esophagus and then withdrawn while noting the position of the probe using a position measuring device. As a result, the location of a colorimetric change at the ora serrate of the esophageal wall can be determined to detect Barrett's metaplasia.

The illuminator preferably includes a first fiber optic waveguide extending through the catheter from a proximal end to a light opening in the distal end of the probe. A light source external to the catheter can then direct the illuminating light into the fiber optic waveguide. An optical reflector axially spaced from but facing toward the distal end of the fiber optic waveguide may be used to redirect and focus the illuminating light in a radially outward direction toward the esophageal wall. The light receiving device preferably includes a second fiber optic waveguide extending coaxially through the catheter around the first fiber optic waveguide. The sensing device is then optically coupled to the proximal end of the second fiber optic waveguide.

The probe may be surrounded by a flexible transparent balloon The probe may illuminate and receive light from a plurality of radial directions at the same time. Alternatively, the probe may receive light from a limited range of radial directions but be rotated to circumferentially scan the esophageal wall. In the event circumferential scanning is used, the catheter may be coupled to a motor and to a rotary encoder or transducer to provide an indication of the angular orientation of the probe.

The position measuring means may comprise a magnetic field generator mounted at a stationary position relative to the esophagus, and a magnetic field sensor mounted on the catheter. As a result, the relative position between the magnetic field generator and the magnetic field sensor corresponds to the position of the probe along the length of the esophagus. Alternatively, the position measuring means may comprise a stationary reference member attached to a patient about the patient's mouth. The relative position between the stationary reference member and the catheter can then be determined to provide an indication of the position of the probe along the length of the esophagus. The position measuring may also comprise a wheel frictionally engaging the catheter and positioned with the rotational axis of the wheel perpendicular to the longitudinal axis of the catheter. As a result, the wheel rotates responsive to axial movement of the catheter, and a rotary encoder coupled to the wheel provides a signal indicative of the axial position of the catheter. An optical system can also be used to keep track of the insertion depth of the catheter.

The sensing device may include a device for simply determining the color of the esophageal wall or it may include a computer or other system coupled to the light receiving device and the position measuring device to provide an image of the esophageal wall and the location of the ora serrate It may be best to use this catheter with a flexible sheath over the portion to be inserted into the esophagus. The sheath would have a transparent tip such that the light introduced would illuminate the esophagus and the returning light would come back through the tip of the sheath to the sensor. This sheath can be installed by slightly inflating the sheath with air pressure as described in U.S. Pat. No. 4,646,722 PROTECTIVE ENDOSCOPE SHEATH AND METHOD OF INSTALLING SAME which is incorporated herein by reference. A similar inflation method can be used to remove the sheath after use. This sheath would be disposable, inexpensive and allow rapid turn around of the catheter, avoiding time consuming and expensive cleaning and disinfection.

DETAILED DESCRIPTION OF THE INVENTION

Figure 1:
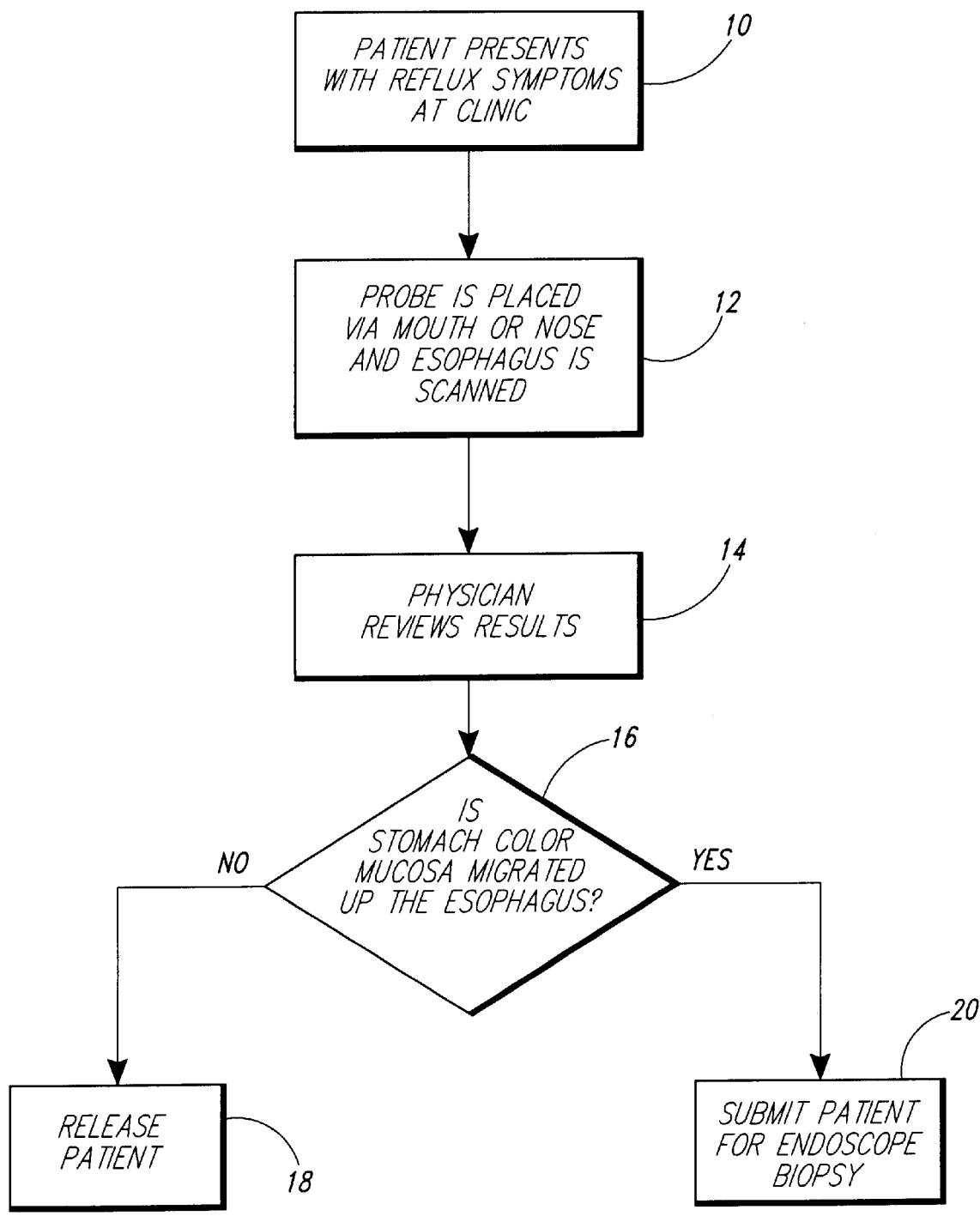
FIG. 1 is a flow chart showing the method of detecting Barrett's metaplasia of the esophagus according to the invention

The manner in which the inventive system can be used to efficiently screen a large populous for Barrett's metaplasia is illustrated in FIG. 1. As mentioned above, patients with reflux symptoms have the highest probability of having Barrett's metaplasia. These patients will present to general practitioners as well as gastrointestinal specialists with reflux symptoms, as shown at step 10 of FIG. 1. As mentioned above, there are currently about 25 million people in the United States who have persistent chronic heartburn and are thus at risk for Barrett's metaplasia. It is feasible to screen this large population at step 12 using the inventive system because the system allows screening to be accomplished quickly and inexpensively by relatively untrained medical practitioners. The results of the screening step 12 can be quickly reviewed by a physician at 14 to determine the location of the pink-to-white junction along the length of the esophagus. The physician makes this determination at 16 and, if the junction is about 39–41 cm from the teeth, releases the patient at 18. Otherwise, the patient is selected for a more rigorous endoscopic examination at 20. Although endoscopic examination is fairly expensive, only about 10% to 15% of the patients screened will require endoscopic examination.

As described in greater detail below, the screening step 12 is accomplished by introducing a small probe via the nose or the mouth into the stomach. This probe, which is mounted at the distal end of a catheter, emits illumination light about the wall of the esophagus adjacent the probe and then senses the color of the adjacent esophageal wall. Once the probe is placed in the stomach about 50 cm from the incisor teeth, the catheter is gradually withdrawn up the esophagus while the depth of the position of the probe in the esophagus is measured. The location at which the pink stomach lining changes to white esophageal lining provides an indication of whether or not the patient has Barrettes metaplasia. The entire scanning step 12 will take very little time and can be accomplished by relatively untrained medical personnel.

Figures 2, 3:
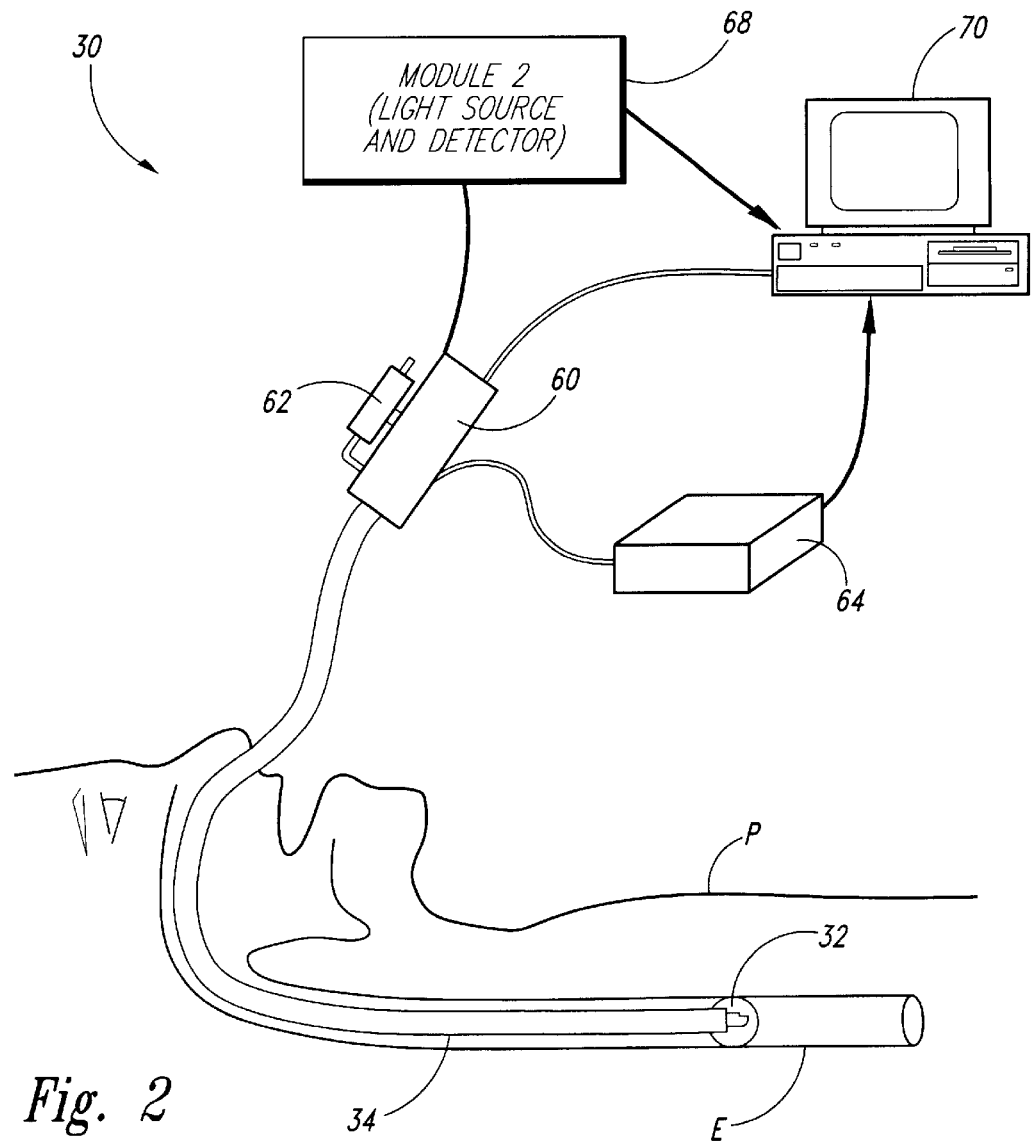
FIG. 2 is a schematic illustrating the basic components of a preferred embodiment of the inventive apparatus in use to detect Barrett's metaplasia of the esophagus.
FIG. 3 is an isometric view of a probe used in the embodiment of FIG. 2.

One of the embodiments of the inventive system is illustrated in FIG. 2. The system 30 includes a probe 32 which is mounted at the distal end of a long flexible catheter 34. The catheter 34 is inserted into the nose or mouth of a patient P and extends through the esophagus E so that the probe 32 is in or near the patient's stomach.

With further reference to FIG. 3, the probe 32 includes a lens/prism holder 36 that is optically coupled to a fiber optic waveguide 38. The fiber optic waveguide 38 is divided into two distinct bundles (not shown in FIG. 3), a first bundle for coupling illumination light to the lens/prism 30 holder 36 and a second bundle coupling light or an image from the lens/prism holder 36. The lens/prism holder 36 includes an optical port 40 through which the esophageal wall E is illuminated and optically examined in a single direction. A transparent flexible balloon 42 surrounds the lens/prism holder 36 to space the esophageal wall E from the lens port 40 and accurately position the probe 32 in the center of the esophagus. The transparent balloon 42 is inflated by coupling pressurized air into it from an external source, as explained in greater detail below.

The lens/prism holder 36 is mounted within a Teflon sleeve 52, which is, in turn, preferably covered with a disposable sheath 54 of a suitable material, such as latex. A cylindrical drive cable 56 is positioned within the Teflon sleeve 52 surrounding the fiber optic waveguide 38. The fiber optic waveguide 38, drive cable 56, Teflon sleeve 52 and sheath 54 together form the catheter 34 that extends from the probe 32 to a location outside of the body of the patient. As explained below, the drive cable is rotated by a suitable device to rotate the lens/prism holder 36 and cause it to circumferentially scan the esophageal wall E. There is sufficient space between the drive cable 56 and the Teflon sleeve 52 to provide for the passage of air into the balloon 42 to selectively inflate the balloon 42.

As best shown in FIG. 2, the catheter 34 extends outside of the body of the patient and terminates in a light-scanning and position-sensing module 60 on which is mounted an inflation syringe 62. The inflation syringe 62 is pneumatically coupled to the inside of the Teflon sleeve 52 to pump air therethrough and inflate the balloon 42. As explained below, the module 60 also includes a motor for rotating the drive shaft 56, an encoder for sensing the rotational position of the drive shaft 56, and a three-dimensional position sensor which detects the position of the module 60 by sensing magnetic fields generated by a conventional magnetic field generator 64. By knowing the three-dimensional position of the module 60, the movement of the module 60 along the axis of the catheter 34 can be determined in order to provide an indication of the movement of the probe 32 through the esophagus.

The light-scanning and position-sensing module 60 is electrically and optically coupled to a light source and detector module 68 which is, in turn, connected to a conventional computer 70. The light source and detector module 68 includes a light source for supplying light to the fiber optic waveguide 38 (FIG. 3), and optical system for receiving light through the fiber optic waveguide 38 reflected from the esophageal wall. The module 68 also couples position information indicative of the axial and rotational position of the probe 32 to the computer 70. The computer 70 then provides information to the medical practitioner in a variety of formats to allow the position of the pink-to-white transition on the esophageal wall to be determined.

Figure 4:
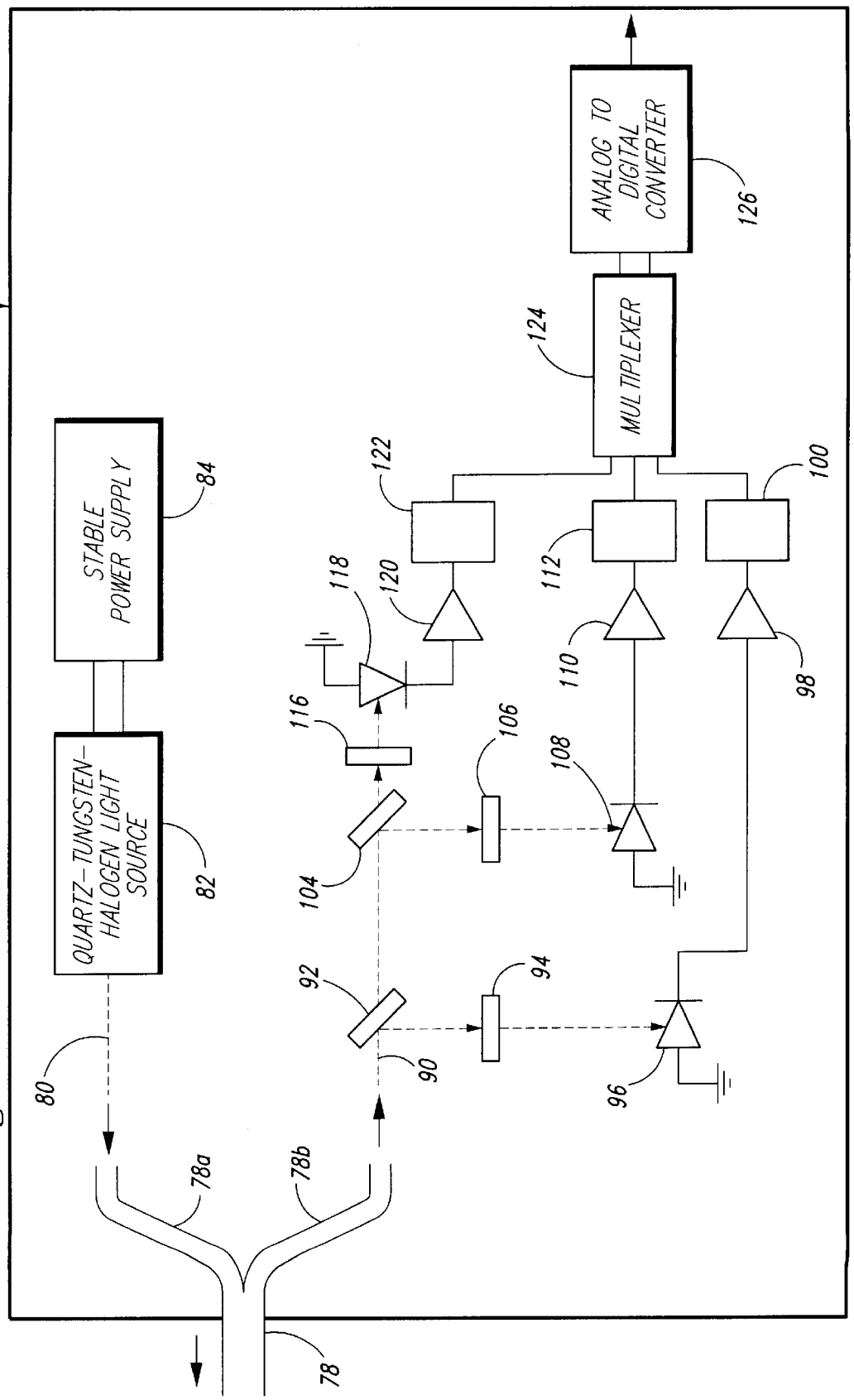
FIG. 4 is a schematic of an illuminating and light detecting module used in the embodiment of FIG. 2.

The light source and detector module 68 is shown in greater detail in FIG. 4. As mentioned above, the fiber optic waveguide 38 is divided into two discrete bundles 38A, 38B, one of which 38A couples illumination light to the probe 32 and the other of which 38B couples light reflected from the esophageal wall. The illumination bundle 38A receives light through a conventional coupling device 80 from a quartz tungsten halogen lamp light source 82 which is driven by a conventional power supply 84. Illuminating devices to apply illuminating light to a fiber optic waveguide are in common use and are thus conventional.

The light reflected from the esophageal wall is processed to provide signals indicative of the intensity of each of several colors. Reflected light from the fiber optic bundle 38B is applied through a conventional coupling mechanism 90 to a 45 degree dichroic blue reflector 92 which reflects the blue portion of the incoming light through a blue corrector filter 94 onto a photodiode 96. The photodiode 96 generates a signal indicative of the amplitude of the incident light in a conventional manner. This signal, which is indicative of the intensity of blue light coupled through the fiber optic bundle 38B, is boosted by an amplifier 98 and sampled by conventional sample and hold circuit 100. Similarly, the remaining light passing through the blue dichroic reflector 92 is incident on a 45 degree dichroic red reflector 104 which reflects the red portion of the light through a red corrector filter 106 and onto a photodiode 108. The signal from the photodiode 108 indicative of the intensity of red light is boosted by an amplifier 110 and applied to a second sample and hold circuit 112. The remaining light passing through the red dichroic reflector 104 passes through a green corrector filter 116 to a third photodiode 118. The signal from the photodiode 118, which is indicative of the intensity of green light, is boosted by a third amplifier 120 and sampled by a sample and hold circuit 122. A multiplexer 124 sequentially selects a sample of one of the colors from the sample and hold circuits 110, 112, 122 and applies the sample to an analog-to-digital converter 126 which outputs a digital value indicative of the color and intensity to the computer 70 (FIG. 2). As explained below, the computer 70 processes this color information in a variety of manners to provide information from which a practitioner determine the location of the pink-to-white transition on the esophageal wall.

Although a white light source and a multiple color (blue, red, green) light source and detector are shown in FIG. 4, it will be understood that a fewer number of colors, including a single color, may be used. The advantage of the multiple color system shown in FIG. 4 is that it can be used to provide full color images of the esophageal wall. However, the pink-to-white transition of the esophageal wall can be detected by only a single color of light, particularly of a color other than red. For example, there will be very little green light reflected from the pink stomach and lower esophageal lining, but green light will be reflected to a substantially greater extent by the white lining of the upper esophagus. Thus, by examining the intensity of reflected green light, the pink-to-white transition of the esophageal lining will be readily apparent by the large increase in intensity of the reflected signal as the probe 32 passes from the pink esophageal lining to the esophageal white lining. In this case a green helium-neon laser could be used as the illumination source.

Figure 5:
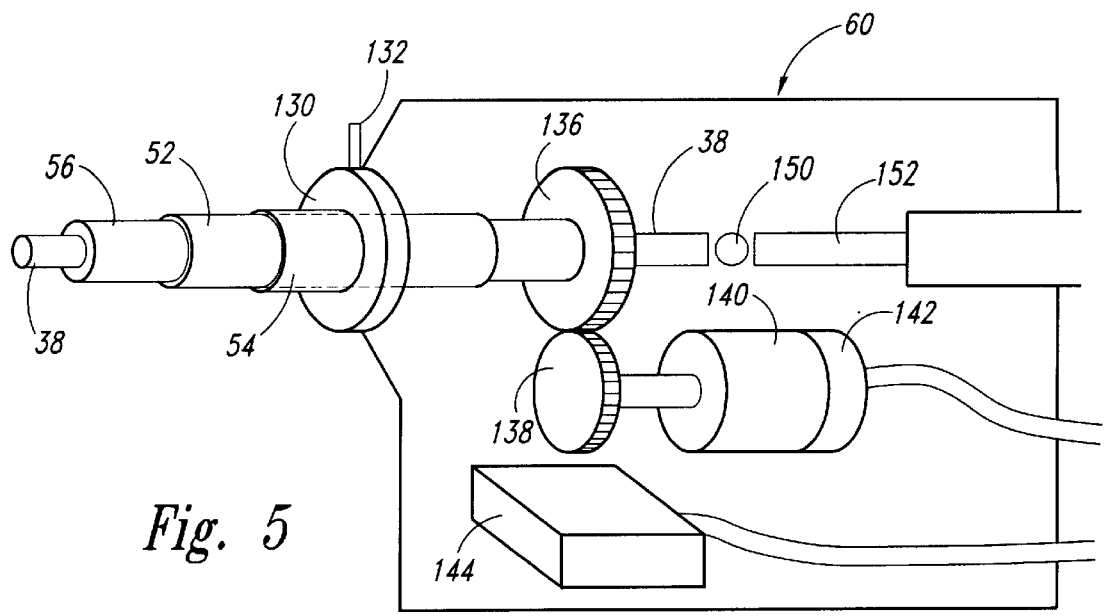
FIG. 5 is a schematic of a position measuring module used in the embodiment of FIG. 2 to measure the position of the probe of FIG. 3 along the length of an esophagus.

The light-scanning and position-sensing module 60 (FIG. 2) is shown in greater detail in FIG. 5. The disposable sheath 54 terminates at the entrance to the module 60 while the Teflon sleeve 52 terminates at an inflation collar 130 to which the inflation syringe 62 (FIG. 2) is coupled through inflation tube 132. As mentioned above, compressed air applied to the inflation tube 132 is coupled in the space between the drive cable 56 and the Teflon sleeve 52 to inflate the transparent balloon 42 (FIG. 3). The sleeve 52 extends into the module 60, and the drive cable 56 projects beyond the inside end of the sleeve 52 and terminates in a pinion gear 136. The pinion gear 136 meshes with a second pinion gear 138 that is coupled to an electric motor 140 a rotary encoder such as and an angular position sensor 142 of conventional design In operation, the motor 140 rotates the probe 32 through the drive cable 56, and the rotational position of the probe 32 is indicated by the output of the angular position sensor 142. A conventional magnetic field detector 144 provides an indication of the position of the module 60 in three dimensions relative to the magnetic field generator 64 (FIG. 2).

The fiber optic waveguide 38 projects beyond the gear 136 and terminates at a spherical lens 150 which couples light from the rotating fiber optic waveguide 38 to a stationary fiber optic waveguide 152. The stationary fiber optic waveguide 152 is coupled to the fiber optic waveguide 78 of the light source and detector module 68 shown in FIG. 4.

Figure 6A:
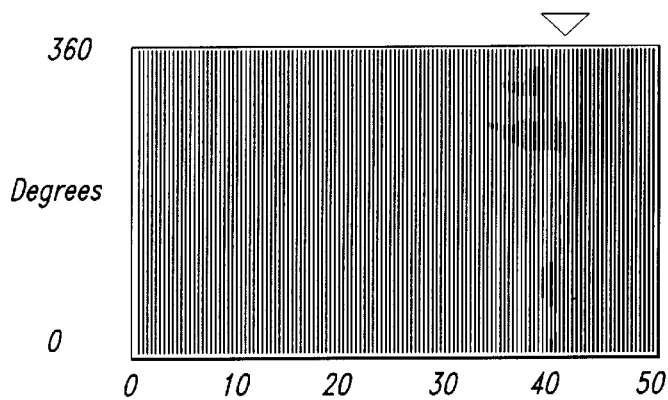
FIG. 6 are drawings of two images obtainable using the embodiment of FIG. 2 to diagnose Barrett's metaplasia of the esophagus.
Figure 6B:
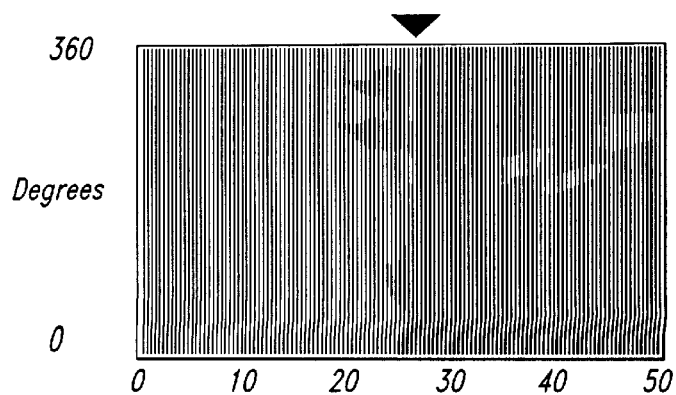

As mentioned above, the computer 70 (FIG. 2) can display the light and positional information from the module 68 in a variety of formats to allow a medical practitioner to determine the location of the pink-to-white transition of the esophageal wall. One format for supplying the light and positional information is a fall color image as shown in FIGS. 6A and 6B. In both of these figures, the rotational position of the probe 32 is shown on the Y axis and the position of the probe 32 along the length of the esophagus is shown in the X axis. The color of each pixel corresponds to the color and intensity of light received by the probe 32 at the corresponding rotational and axial position. The image shown in FIGS. 6A and 6B can be obtained by simply recording in suitable memory sets of data for each incremental axial position of the probe 32. Each set of data includes for each angular position of the probe 32 the intensity of the blue, red and green samples output by the analog-to-digital converter 126. The manner in which a computer can perform this function is conventional and thus, in the interest of brevity, not explained herein. The pink-to-white transition of the esophageal wall is shown in FIG. 6A as occurring at about 40 cm, thus indicating that the patient does not have Barrett's metaplasia FIG. 6B shows the pink-to-white transition of the esophageal lining occurring at about 28 cm from the teeth of the patient, thus indicting that the patient may have Barrett's metaplasia and should be screened further by endoscopic examination and biopsy as illustrated at 20 in FIG. 1.

Figure 7:
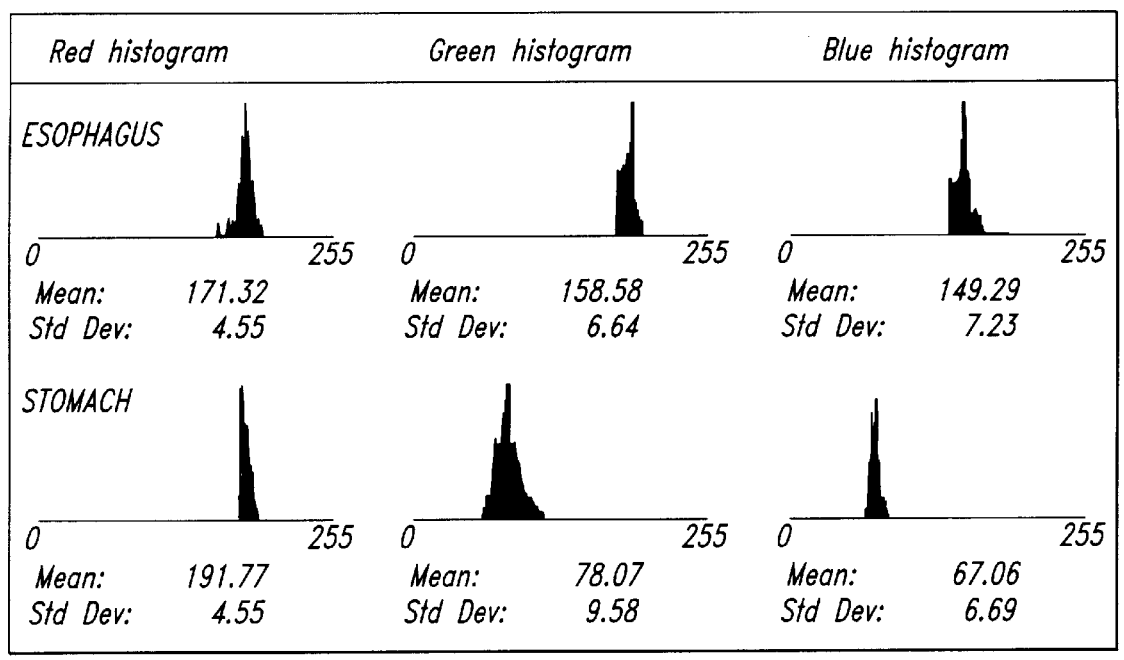
FIG. 7 is a drawing showing color histograms obtainable using the embodiment of FIG. 2 to diagnose Barrett's metaplasia of the esophagus.

The information stored in the computer 70 to provide the images shown in FIGS. 6A and 6B can also be used to calculate and display histograms as shown in FIG. 7. Each of the histograms shows the intensity of a specific color of light (Y axis) as a function of the axial position of the probe 32 (X axis). The histograms shown in FIG. 7 do not provide any information about color as a function of the rotational position of the probe 32. Instead, the histogram information at each axial position (shown on the X axis) is an average of the intensities at all sampled radial positions. The histograms of FIG. 7 compare the blue, green and red reflected light above (upper set) and below (lower set) the ora serrata. In FIG. 7, the red light characteristics remain the same (since red is reflected equally from white and pink tissues) but the green and blue content of the reflected light is different above and below the ora serrata. This difference makes detection of the ora serrata easier with blue or green light compared to red or white light.

Figure 8:
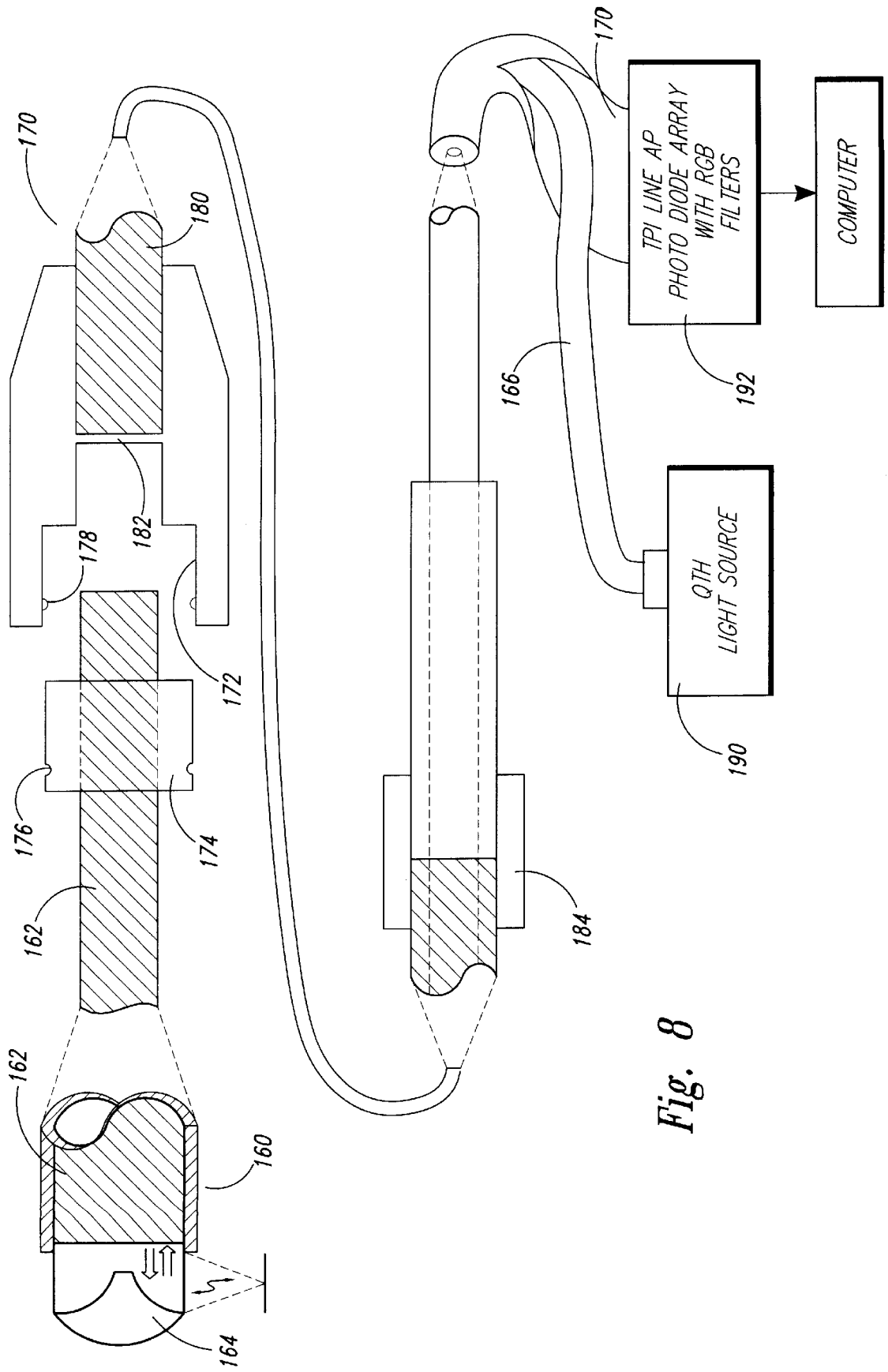
FIG. 8 is a schematic illustrating the basic components of an alternative embodiment of the inventive apparatus in use to detect Barrett's metaplasia of the esophagus.
Figure 9A:
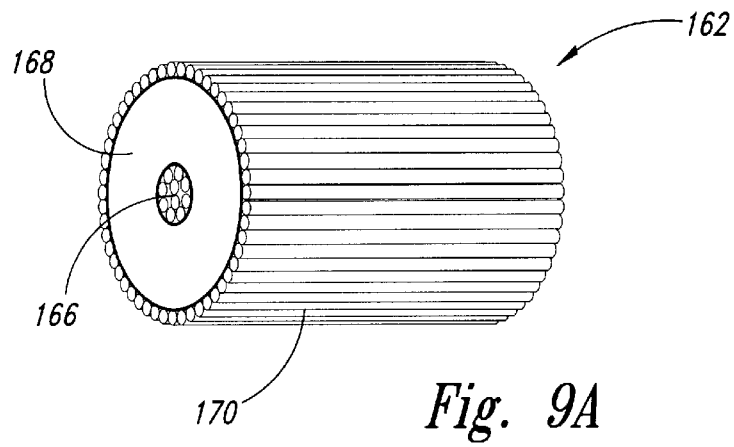
FIG. 9 is a schematic illustrating the manner in which fiber optic waveguides used in the embodiment of FIG. 7 are arranged to deliver and return light from the esophageal wall.
Figure 9B:
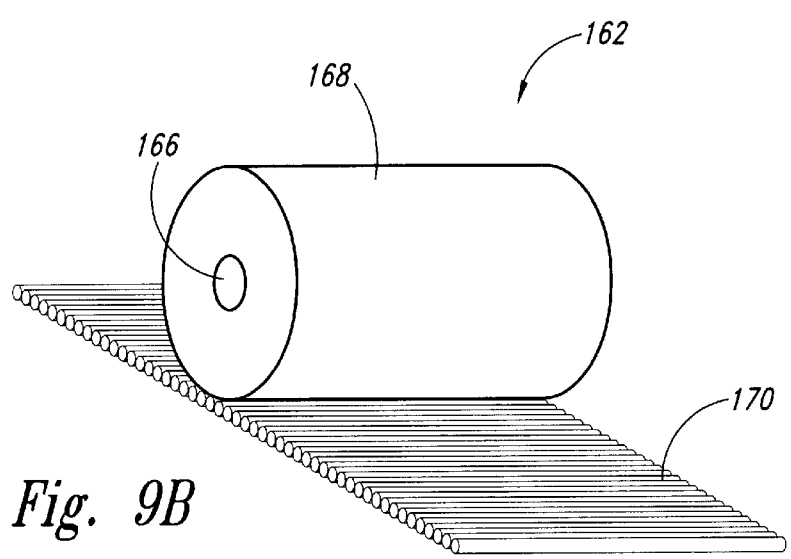

An alternative embodiment of a system for detecting Barrett's metaplasia is shown in FIGS. 8 and 9. The embodiment of FIGS. 8 and 9 differs from the embodiment of FIGS. 2-5 in that it utilizes a probe 160 that simultaneously scans in 360° and thus need not be mechanically rotated to image entirely around the probe 160. The embodiment of FIGS. 8 and 9 uses an imaging and illumination bundle 162 which, as illustrated in FIGS. 9A and 9B, consists of an inner fiber optic bundle 166 surrounded by a concentric spacer 168 which is, in turn, surrounded by a plurality of optical fibers arranged in a cylinder 170. The inner light bundle 166 is used to conduct illuminating light to the probe 160, while each of the optical fibers 170 conducts reflected light from a discrete radial direction from the probe 160.

As best illustrated in FIG. 8, the imaging bundle 162 terminates behind a generally conical mirror 164 which directs and focuses light from the illuminating bundle 166 in a 360° circumferential arc around the catheter. Light reflected from the esophageal wall is then reflected by the conical mirror 164 to the optical fibers 170. Since the optical fibers 170 extend around the circumference of the bundle 162, they each receive reflected light from a discrete angular position about the probe 160.

Figure 9C:
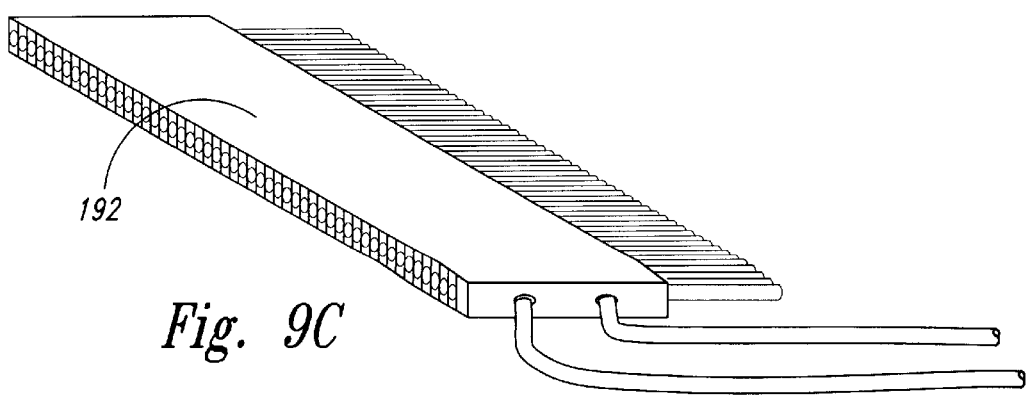

The proximal end of the imaging and illumination bundle 162 fits into a coupling member 170 so that the fiber optic bundle 162 and probe 160 can be easily replaced. The coupling member 170 includes a cylindrical recess 172 that receives a collar 174 secured about the proximal end of the imaging and illumination bundle 162. An annular groove 176 formed in the collar 174 receives a resilient ring 178 lining the inside of the cylindrical cavity 172 to lock the collar 174 in position within the cavity 172. When the collar 172 is in position in the cavity 172, the distal end of the imaging and illumination bundle 162 abuts an imaging and illumination fiber optic bundle 180 positioned in the coupling member 170 through an index matching gel 182. The fiber optic bundle 180 extends to a transition member 184 in which the optical fibers 170 are separated from the illuminating light bundle 166. The illuminating light bundle 166 is coupled to a conventional light source 190, while the optical fibers 170 are arranged in a flat configuration and coupled to a photodiode array 192, which is best illustrated in FIG. 9C. The photodiode array 192 preferably includes a sensing cell for each optical fiber 170, with each cell containing three light sensors receiving light through respective red, green and blue filters. As mentioned above, multiple light sensors allow for full color imaging of the esophageal wall. However, as with the embodiment of FIGS. 2–5, single color imaging may be used. Also, although 360° scanning of the esophageal wall is preferred, it will be understood that multiple direction (e.g., 0°, 90°, 180° and 270°) or single direction scanning may also be used.

It should be understood that a technique that does not rely on circumferential scanning may be used. In this technique a segment of the esophageal wall is illuminated over the full 360° as illustrated in FIG. 8. All of the detected light is then passed through a single color separation device as illustrated in FIG. 4. The resultant outputs will be the average of red, green and/or blue values around the circumference of the illuminated segment of the esophageal wall.

Figure 10:
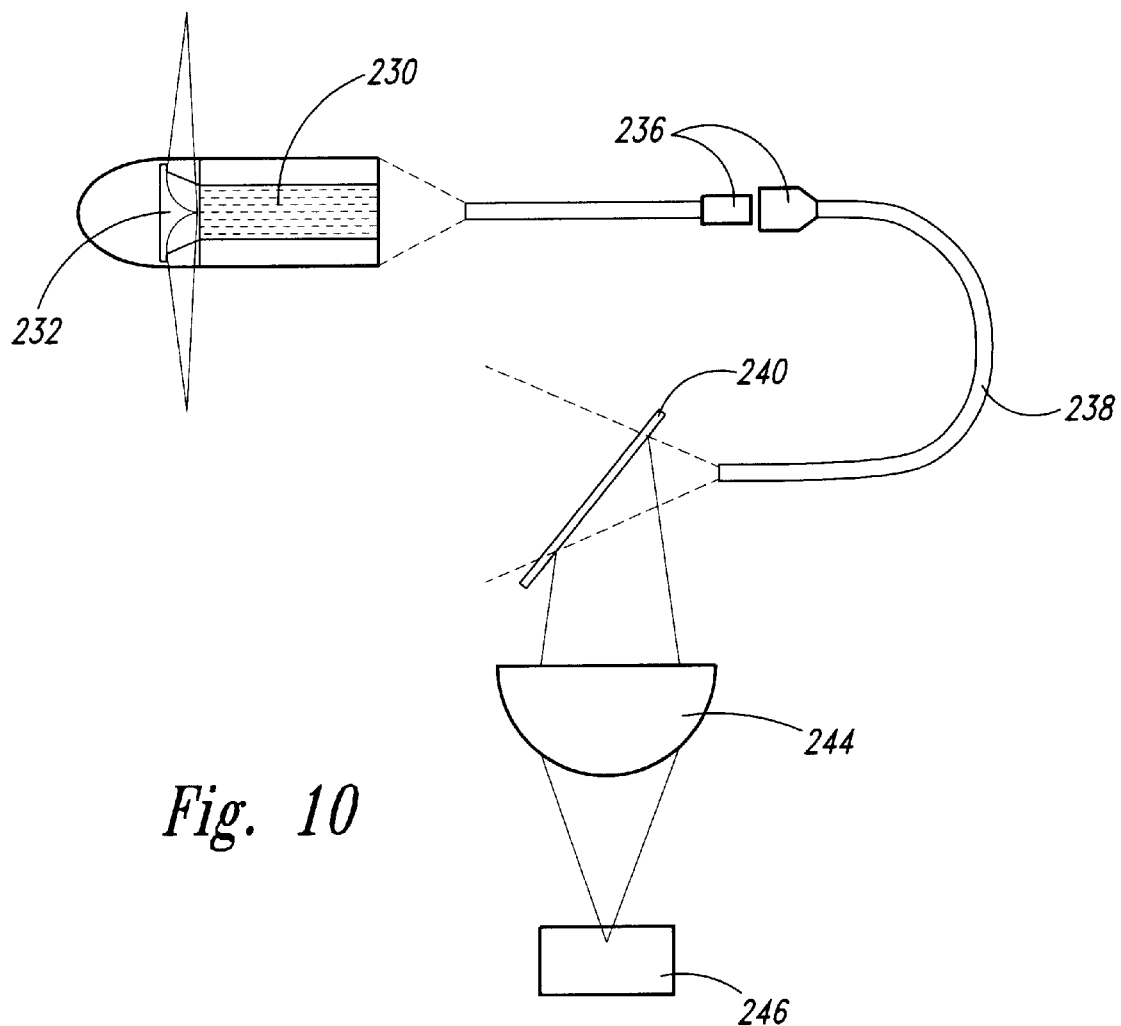
FIG. 10 is a schematic view of an alternative embodiment of the inventive apparatus to detect Barrett's metaplasia.

A simplified embodiment of that shown in FIGS. 8 and 9 that is suitable for this non-scan technique is shown in FIG. 10. The fundamental difference between this system and the other described systems is that only a single optic fiber 230 is used in the probe. The illumination light exiting the fiber 230 is focused and directed radially from the axis of the fiber by an essentially conical reflector 232 similar to the reflector 164 of FIG. 8. Light reflected from the esophageal wall is directed back into the single optical fiber 230 by the reflector 232. The proximal end of the optical fiber 230 is terminated in a connector 236 that, with the exception that it contains only a single optical fiber, is identical to the coupling device 170-182 described in FIG. 8. Both the illumination light and the light reflected from the esophageal wall pass through a single optical fiber 238 extending from the connector 236. The reflected light exiting the optical fiber 238 is directed onto a reflective beam splitter 240. Fifty percent or more of the light is deflected away from the axis of the optical fiber 238 and through a lens 244 where it is input to a color separator 246 identical to that described in FIG. 4. The illumination light is focused on the input face of the optical fiber 238 in the common manner, but the reflective beam splitter 240 is in the optical path. The light reflected off of the beam splitter 240 will be lost for illumination purposes.

The single optical fiber device shown in FIG. 10 has the disadvantage that only fifty percent of the illumination source light and fifty percent of the reflected return light is usable, the other fifty percent being directed away from a useful path by the beam splitter 240. There are, however, several advantages. The primary and fundamentally most important is that the optical system is a confocal system. The focus for illumination has to be the focus for detection. Additional advantages are the ease of fabrication, less stringent alignment requirements than multiple optical fibers, and the total area of a single fiber is optically usable while a bundle of equivalent diameter has dead areas between the individual fibers.

Figure 11:
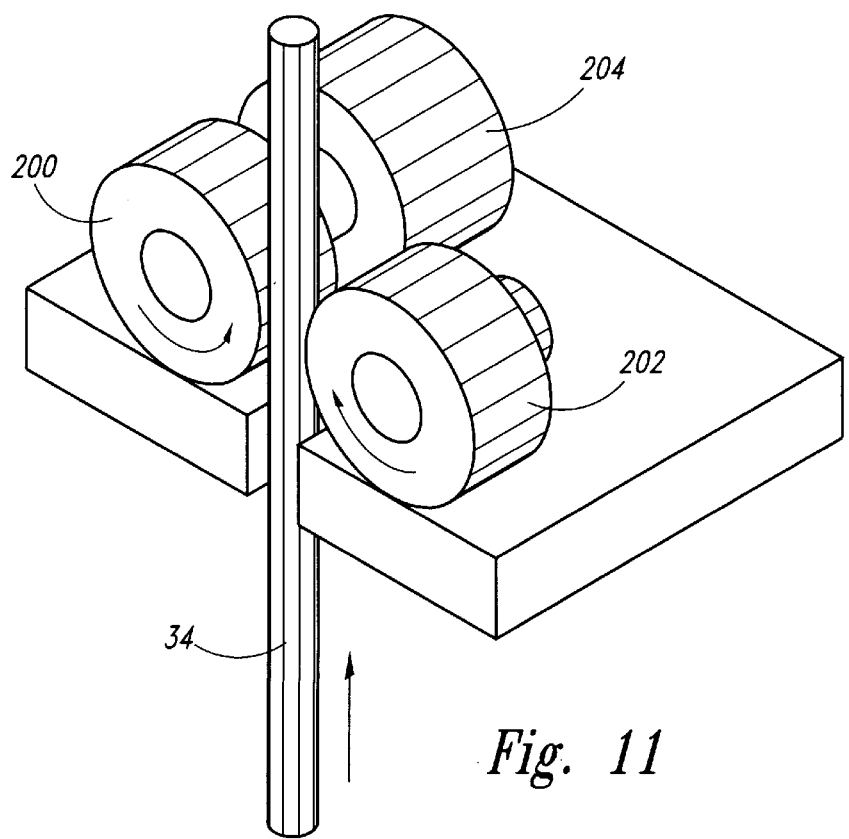
FIG. 11 is a schematic illustrating an alternative technique for measuring the position of the probe of FIG. 3 along the length of an esophagus.

With the probe embodiment shown in FIG. 11, as with others, only a single color such as green may be used. In that case, the light source may have a green filter on it or only a green light filter would be used with a single photodiode or other photo sensor. Furthermore, instead of a computer being used as a display device, other means of sensing color or displaying an image may be used. For example, a display light may turn on when the adequate green light has been received indicating the probe has crossed the ora serrata during a linear scan of the esophageal wall. A further simplified system would have distance markings on the probe somewhat similar to a ruler. In this case the user would just visibly monitor the markings as the probe is withdrawn. When the display indicates the ora serrata has been reached, the user would just record the distance from the teeth that the sensor is located. A complete simplified system could use the single fiber system described above, a single color, length markings on the probe, and a simple indicator that turns on when the ora serrata has been crossed.

A variety of techniques may be used to provide an indication of the axial position of the probe 32 (FIG. 2) along the length of the esophagus. As illustrated in FIG. 11, the catheter 34 is compressed between a pair of friction wheels 200, 201 so that the wheels 200, 201 rotate with axial movement of the catheter 34. One of the friction wheels 200 is mechanically coupled to a conventional angle sensor 204 which provides an electrical signal indicative of the rotation of the wheel 200 in a conventional manner. The angle sensor 204 thus provides an indication of the axial position of the catheter 34. Other position sensing techniques may also be used as desired For example, a device could be placed in the teeth of a patient which would interact with a mechanical or electrical member extending along the probe catheter to provide an indication of the axial position of the probe tip. Although an electrical sensor could be used, it will be also understood that optical position sensing using markings on the outer surface of the catheter may also be used. Other position measuring techniques, as well as other forms of processing information indicative of the color of the esophageal wall may also be used.

We claim:

1. A system for use in detecting Barrett's metaplasia of the esophagus, comprising:
   a flexible catheter;
   a probe mounted at a distal end of said flexible catheter, said probe having an illuminator and a light receiving device each of which are directed radially outwardly to illuminate the wall of an esophagus into which said probe has been inserted and receive light from the esophageal wall;
   a position measuring device measuring the position of said probe along the length of said esophagus; and
   a light sensing device coupled to said light receiving device, said light sensing device providing an indication of the color of the esophageal wall whereby Barrett's metaplasia of the esophagus can be detected based on a colorimetric change in the esophagus as sensed through said sensing device at a location along the length of the esophageal wall indicated by said position measuring device.

2. The system of claim 1 wherein said light from said illuminator is free of any significant red components.

3. The system of claim 2 wherein said light from said illuminator is green.

4. The system of claim 2 wherein said light from said illuminator is blue.

5. The system of claim 1 wherein said light from said illuminator is red, blue, and green.

6. The system of claim 1 wherein said illuminator and said light receiving device are each directed radially outward in a plurality of directions to illuminate said esophageal wall and receive light from a plurality of circumferential locations on said esophageal wall.

7. The system of claim 6 wherein said illuminator comprises a first fiber optic waveguide extending through said catheter from a proximal end of said catheter to a light opening in said probe, and a light source external to said catheter directing illuminating light into said fiber optic waveguide.

8. The system of claim 7 wherein said light receiving device comprises a second fiber optic waveguide extending from an image port in said probe to a viewing device at the proximal end of said catheter, said viewing device providing an output signal indicative of a characteristic of said light.

9. The system of claim 8 wherein said viewing device includes a filter receiving said light from said second fiber optic waveguide, and a light detector positioned adjacent said filter to receive light passing therethrough, said light detector generating said output signal as a function of the amplitude of light received by said light detector so that said output signal is indicative of the intensity of light corresponding to the wavelength of said filter.

10. The system of claim 8 wherein said light receiving device receives light from a limited range of radial directions at the same time, and wherein said catheter further includes a hollow flexible drive cable surrounding said first fiber optic waveguide, and wherein said system further includes scan means for rotating the proximal end of said drive cable so that said probe is rotated about the longitudinal axis of said catheter to scan an esophagus into which said probe has been inserted.

11. The system of claim 10 wherein said probe further includes a flexible transparent balloon surrounding said probe, and wherein said catheter further includes an outer sheath loosely surrounding said drive cable to form a lumen between said drive cable and sheath, said lumen communicating with the interior of said balloon so that said balloon can be inflated by injecting pressurized fluid into the proximal end of said lumen.

12. The system of claim 10 wherein said scan means comprise a motor mechanically coupled to said drive cable, and a rotary encoder to provide an indication of the rotational position of said probe.

13. The system of claim 1 wherein said position measuring device comprises a wheel having its periphery frictionally engaging said catheter, said wheel being positioned with the rotational axis of said wheel perpendicular to the longitudinal axis of said catheter so that said wheel rotates responsive to axial movement of said catheter, and a rotary encoder coupled to Said wheel to provide a signal indicative of the axial position of said catheter.

14. The system of claim 1 wherein said sensing device comprises a visual display coupled to said probe and said position measuring device, said visual display providing a visual image of said esophageal wall.

15. The system of claim 14 whereing said visual display shows the length of said esophageal wall along one axis of a visual display screen, and the circumference of said esophageal wall along an orthogonal axis of said visual display screen.

16. A system for use in detecting Barrett's metaplasia of the esophagus, comprising:

a flexible catheter;

a probe mounted at a distal end of the flexible catheter, the probe having an illuminator and a light-receiving device each of which are directed radially outwardly to illuminate the wall of an esophagus into which the probe has been inserted and receive light from the esophageal wall, the probe further including a flexible transparent balloon surrounding the probe, and wherein the catheter further includes a fluid passage communicating with the interior of the balloon so that the balloon can be inflated by injecting pressurized fluid into the fluid passage at a proximal end thereof, a position-measuring device measuring the position of the probe along the length of the esophagus; and a light-sensing device coupled to the light-receiving device, the light-sensing device providing an indication of the color of the esophageal wall whereby Barrett's metaplasia of the esophagus can be detected based on a colorimetric change in the esophagus as sensed through the sensing device at a location along the length of the esophageal wall indicated by the position-measuring device.

17. A system for use in detecting Barrett's metaplasia of the esophagus, comprising:

a flexible catheter;

a probe mounted at a distal end of the flexible catheter, the probe having an illuminator and a light-receiving device each of which are directed radially outwardly to illuminate the wall of an esophagus into which the probe has been inserted and receive light from the esophageal wall;

a position-measuring device measuring the position of the probe along the length of the esophagus, the position-measuring device comprising a magnetic field generator adapted to be mounted at a stationery position relative to the position of the esophagus, and a magnetic field sensor mounted on the catheter so that the relative position between the magnetic field generator and the magnetic field sensor corresponds to the position of the probe along the length of an esophagus into which the probe has been inserted; and a light-sensing device coupled to the light-receiving device, the light sensing device providing an indication of the color of the esophageal wall whereby Barrett's metaplasia of the esophagus can be detected based on a calorimetric change in the esophagus as sensed through the sensing device at a location along the length of the esophageal wall indicated by the position-measuring device.

* * * * *